(12) United States Patent
Desenne

(10) Patent No.: US 7,150,765 B2
(45) Date of Patent: Dec. 19, 2006

(54) FATTY ACID-FREE LIQUID DYE COMPOSITION COMPRISING AT LEAST ONE OXIDATION BASE AND 2-METHYL-1, 3-PROPANEDIOL, DYEING PROCESS, AND DEVICE

(75) Inventor: Patricia Desenne, Bois Colombes (FR)

(73) Assignee: L'Oreal S.A. (FR)

( * ) Notice: Subject to any disclaimer, the term of this patent is extended or adjusted under 35 U.S.C. 154(b) by 337 days.

(21) Appl. No.: 10/887,922

(22) Filed: Jul. 12, 2004

(65) Prior Publication Data

US 2005/0050649 A1 Mar. 10, 2005

Related U.S. Application Data

(60) Provisional application No. 60/488,806, filed on Jul. 22, 2003.

(30) Foreign Application Priority Data

Jul. 11, 2003 (FR) .................. 03 08545

(51) Int. Cl.
*A61K 7/13* (2006.01)

(52) U.S. Cl. .............. 8/405; 8/406; 8/408; 8/410; 8/411; 8/412; 8/426; 8/437; 8/611

(58) Field of Classification Search ............ 8/405, 8/406, 408, 410, 411, 412, 426, 437, 611
See application file for complete search history.

(56) References Cited

U.S. PATENT DOCUMENTS

| 2,528,378 | A | 10/1950 | Mannheimer |
|---|---|---|---|
| 2,781,354 | A | 2/1957 | Mannheimer |
| 4,003,699 | A | 1/1977 | Rose et al. |
| 5,061,289 | A | 10/1991 | Clausen et al. |
| 5,380,340 | A | 1/1995 | Balzer et al. |
| 5,766,576 | A | 6/1998 | Balzer et al. |
| 6,099,592 | A | 8/2000 | Burande et al. |
| 6,099,593 | A | 8/2000 | Terranova et al. |
| 6,338,741 | B1 | 1/2002 | Burande et al. |
| 6,645,258 | B1 | 11/2003 | Burande et al. |
| 2002/0004955 | A1 | 1/2002 | Lang et al. |
| 2002/0046431 | A1* | 4/2002 | Laurent et al. .......... 8/405 |
| 2002/0050013 | A1 | 5/2002 | Burande et al. |
| 2003/0019051 | A9 | 1/2003 | Burande et al. |
| 2003/0074747 | A1 | 4/2003 | Vuarier et al. |
| 2004/0083558 | A1 | 5/2004 | Fessmann et al. |

FOREIGN PATENT DOCUMENTS

| DE | 2 359 399 | 6/1975 |
|---|---|---|
| DE | 3 843 892 A | 6/1990 |
| DE | 4 133 957 A1 | 4/1993 |
| DE | 195 43 988 A1 | 5/1997 |
| EP | 0 962 220 | 12/1999 |
| EP | 1 179 336 | 2/2002 |
| EP | 1 279 395 | 1/2003 |
| FR | 2 733 749 A1 | 11/1996 |
| FR | 2 750 048 A1 | 12/1997 |
| FR | 2 817 551 A1 | 6/2002 |
| GB | 1 026 978 | 4/1966 |
| GB | 1 153 196 | 5/1969 |
| JP | 91-10659 | 4/1997 |
| JP | 88-169 571 | 7/1998 |
| WO | WO 94/08969 A1 | 4/1994 |
| WO | WO 94/08970 A1 | 4/1994 |
| WO | WO 96/15765 A1 | 5/1996 |

OTHER PUBLICATIONS

"Handbook of Surfactant", by M.R. Porter, published by Blackie & Son (Glasgow and London), 1991, pp. 116-178.
English language Derwent Abstract of JP 91- 10659, Apr. 28, 1997.
English language Derwent Abstract of JP 88-169 571, Jul. 7, 1998.
French Search Report, dated Feb. 16, 2004.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

A liquid dye composition, free of fatty acids and fatty acid salts, comprising at least one oxidation base and 2-methyl-1,3-propanediol; a ready-to-use composition comprising the liquid dye composition and at least one oxidizing agent; a process for dyeing human keratin fibers using the liquid dye composition; and a device comprising the liquid dye composition.

34 Claims, No Drawings

FATTY ACID-FREE LIQUID DYE COMPOSITION COMPRISING AT LEAST ONE OXIDATION BASE AND 2-METHYL-1, 3-PROPANEDIOL, DYEING PROCESS, AND DEVICE

This application claims benefit of U.S. Provisional Application No. 60/488,806, filed Jul. 22, 2003.

Disclosed herein is a liquid dye composition, free of fatty acids or of fatty acid salts, comprising at least one oxidation dye and 2-methyl-1,3-propanediol, a ready-to-use composition comprising the liquid dye composition, a process for dyeing human keratin fibers using the liquid dye composition and a device comprising the liquid dye composition.

It is known practice to dye keratin fibers, such as human hair, with dye compositions comprising oxidation dye precursors, generally known as "oxidation bases", such as ortho- or para-phenylenediamines, ortho- or para-aminophenols, and heterocyclic bases.

Oxidation dye precursors are compounds that are initially uncolored or only weakly colored, which develop their dyeing power on hair in the presence of oxidizing agents, leading to the formation of colored compounds. The formation of these colored compounds results either from an oxidative condensation of the oxidation bases with themselves or from an oxidative condensation of the oxidation bases with coloration modifiers, or "couplers. Couplers are generally present in dye compositions used in oxidation dyeing and may be chosen, for example, from meta-phenylenediamines, meta-aminophenols, meta-diphenols, and certain heterocyclic compounds.

The variety of molecules used, which include on the one hand the "oxidation bases" and on the other hand the "couplers", may allow a very wide range of colors to be obtained.

These oxidation bases and couplers may be reacted in supports that allow them to be applied to the keratin fibers after mixing with an oxidizing agent.

There are essentially two types of support: creams or liquids, which may be differentiated, for example, by their respective viscosity range and their composition. For example, when a cream is mixed with an oxidizing composition, the resulting composition must be fluidized enough to allow homogeneous mixing of the constituent components of these two compositions and to allow for an easy application to hair. However, the resulting composition should not lose too much viscosity and should not run beyond the area to be dyed. On the other hand, a support in liquid form must be able, once mixed with the oxidizing composition, to produce a composition whose viscosity is higher so as to allow application under suitable conditions.

As mentioned previously, disclosed herein are dye compositions in liquid form.

Liquid supports, for example, may have the advantage of being easier to pack and easier to use, and, for example, the operation of mixing with an oxidizing composition may be easier.

Further, liquid supports may constitute an advantageous alternative to cream supports, which may, in certain cases, pose problems of viscosity stabilization during storage.

Liquid supports quite often comprise a solvent chosen, for example, from alcohols and ethers thereof.

Although such solvents make it possible to obtain dye compositions, which, when mixed with oxidizing compositions, give good results, it is desired, however, to further improve their performance qualities.

It has moreover been found that the presence of fatty acid soaps could result in at least one cosmetic drawback or limit the working pH range of the composition.

Finally, in certain cases, the dye compositions may have a cloudy appearance at low temperature, due to insufficient homogeneity of the composition. The consequence is that, in the more or less long term, depending on the storage conditions, phase separation of the dye composition may be observed.

Thus, disclosed herein are dye compositions in liquid form that overcome at least one of these drawbacks and that can produce dyeing results that may be satisfactory, or even improved. At least one of these aims and others are achieved by the liquid dye composition disclosed herein.

Accordingly, disclosed herein is a liquid dye composition comprising at least one oxidation dye and 2-methyl-1,3-propanediol, wherein the at least one liquid dye composition is free of fatty acids and of fatty acid salts.

Further disclosed herein is a ready-to-use composition comprising at least one liquid dye composition comprising at least one oxidation dye, 2-methyl-1,3-propanediol, and at least one oxidizing agent, wherein the liquid dye composition is free of fatty acids and of fatty acid salts.

Even further disclosed herein is a process for dyeing human keratin fibers comprising applying to the fibers (a) at least one liquid dye composition comprising at least one oxidation dye and 2-methyl-1,3-propanediol, wherein the liquid dye composition is free of fatty acids and of fatty acid salts and (b) at least one oxidizing composition comprising at least one oxidizing agent, wherein the at least one oxidizing composition is mixed with the at least one liquid dye composition at the time of application or is applied sequentially without intermediate rinsing.

Further disclosed herein is a multi-compartment device for dyeing human keratin fibers, comprising at least one first compartment comprising at least one liquid dye composition comprising at least one oxidation dye and 2-methyl-1,3-propanediol, wherein the liquid dye composition is free of fatty acids and of fatty acid salts, and at least one second compartment comprising at least one oxidizing composition comprising at least one oxidizing agent.

Thus, the liquid dye composition disclosed herein may be stable on storage, in the sense that its viscosity does not change significantly and no phase separation is observed over time.

In addition, the composition obtained after the at least one liquid dye composition is mixed with the at least one oxidizing composition may have a viscosity that is adapted during the application, this viscosity being conserved throughout the period of application of the product to the fibers.

Finally, the colorations obtained by using the liquid dye compositions may be intense, chromatic, and sparingly selective, and the cosmetic properties of the resulting fibers may not be substantially degraded.

However, other aims and characteristics of the disclosed embodiments will emerge more clearly on reading the description and the examples that follow.

In the description, unless otherwise indicated, the limits of the ranges of values are considered as being included within these ranges.

As has been mentioned previously, the dye composition disclosed herein is in liquid form. It should be noted that the liquid dye composition does not comprise an oxidizing agent.

As used herein, the term "liquid composition" means a composition which, at a temperature of 25° C. under 1 atmosphere, has a viscosity of less than 150 cPs, measured using a RheoStress 1 rheometer, under a shear rate of 200 s$^{-1}$.

Moreover, in one embodiment, the liquid dye composition is a clear liquid. For example, the composition is in the form of a transparent isotropic liquid. The composition may have, for example, a turbidity ranging from 60 to 600 NTU and, for example, from 70 to 400 NTU (measurement performed using a Hach model 2100 P portable turbidimeter at 25° C.).

The liquid dye composition disclosed herein is also free of fatty acids and of fatty acid salts. As used herein, the term "fatty acid" means carboxylic acids comprising a saturated or unsaturated, linear or branched hydrocarbon-based radical comprising from 8 to 30 carbon atoms, optionally bearing at least one hydroxyl radical.

As used herein, the term "fatty acid salt" means alkali metal or alkaline-earth metal salts of the above-mentioned fatty acids, for example, sodium, potassium or magnesium salts.

As noted above, the liquid dye composition disclosed herein comprises 2-methyl-1,3-propanediol.

The 2-methyl-1,3-propanediol may be present in an amount ranging from 0.5% to 20% by weight, relative to the total weight of the liquid dye composition. In one embodiment, the 2-methyl-1,3-propanediol is present in an amount ranging from 5% to 20% by weight relative to the total weight of the liquid dye composition and, even further, for example, from 10% to 18% by weight, relative to the total weight of the liquid dye composition.

The composition may also comprise at least one polyol chosen from polyols comprising at least two hydroxyl radicals, other than 2-methyl-1,3-propanediol, and polyol monoethers and polyethers; wherein the polyols comprising at least two hydroxyl radicals and the polyol portion of the polyol monoethers and polyethers comprise at least one radical chosen from saturated and unsaturated, linear and branched hydrocarbon-based radicals comprising from 3 to 50 carbon atoms and, for example, from 3 to 10 carbon atoms, optionally interrupted with at least one oxygen atom.

For example, the at least one polyol may be chosen from pinacol (2,3-dimethyl-2,3-butanediol), glycerol (1,2,3-propanetriol), 1,2,3-butanetriol, 3-methyl-1,3,5-pentanetriol, 1,2,4-butanetriol, propylene glycol, dipropylene glycol, 1,5-pentanediol, 3-methyl-1,5-pentanediol, neopentyl glycol (2,2-dimethyl-1,3-propanediol), isoprene glycol (3-methyl-1,3-butanediol), and hexylene glycol (2-methyl-2,4-pentanediol).

In one embodiment, the at least one polyol, if present, is chosen from glycerol, propylene glycol, dipropylene glycol, and hexylene glycol.

The polyol monoethers and polyethers may or may not comprise at least one hydroxyl group. The polyol monoethers and polyethers may comprise at least one radical, which may be identical or different, which blocks the hydroxyl functional group(s) of the polyol and which comprises, for example, from 1 to 30 carbon atoms. In one embodiment, the at least one radical blocking the hydroxyl functional group (s) is chosen from alkyl radicals. In one embodiment, the total number of carbon atoms of each of the monoethers and polyethers ranges from 4 to 50.

For example, if present, the at least one polyol may be present in an amount ranging from 0.1% to 20% by weight, relative to the total weight of the liquid dye composition and, for example, from 0.2% to 10% by weight, relative to the total weight of the liquid dye composition.

Finally, again in the case where it is present, the at least one polyol may be present in the liquid dye composition such that the weight ratio of the 2-methyl-1,3-propanediol to the at least one polyol is greater than 1 and, for example, is less than or equal to 10.

The liquid dye composition may also comprise at least one short-chain monoalcohol. For example, the at least one short-chain monoalcohol may comprise at least one chain chosen from linear and branched alkyl chains, comprising from 2 to 8 carbon atoms. Examples of compounds of this type include ethanol and isopropanol.

If present, the at least one short-chain monoalcohol is present in an amount ranging from 0.1% to 20% by weight, relative to the total weight of the liquid dye composition and, for example, from 0.2% to 20% by weight, relative to the total weight of the liquid dye composition.

It should be noted that the at least one polyol and the at least one monoalcohol are present in an amount in the liquid dye composition such that the composition is a clear liquid in the sense indicated previously.

It should be noted that, in one embodiment, the liquid dye composition comprises water.

The liquid dye composition also comprises at least one oxidation dye.

More specifically, the at least one oxidation dye is chosen from oxidation bases and couplers.

The oxidation bases may be chosen from those conventionally used in the dyeing of keratin fibers.

For example, the oxidation bases may be chosen from at least one of ortho-phenylenediamines, para-phenylenediamines, double bases, ortho-aminophenols, para-aminophenols, heterocyclic bases, and addition salts thereof with an acid or an alkaline agent.

Examples of the oxidation bases include the following:

(I) Para-phenylenediamines of formula (I) below and addition salts thereof with an acid:

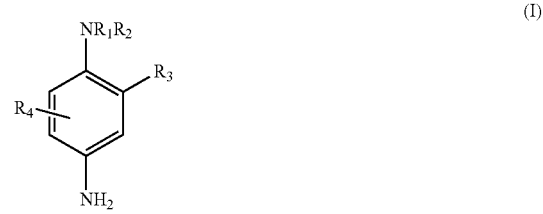

wherein:

$R_1$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with at least one group chosen from nitrogenous, phenyl, and 4'-aminophenyl groups;

$R_2$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with at least one nitrogenous group;

$R_1$ and $R_2$ may also form, with the nitrogen atom that bears them, a 5- or 6-membered nitrogenous heterocycle optionally substituted with at least one group chosen from alkyl, hydroxyl, and ureido groups;

$R_3$ is chosen from a hydrogen atom, halogen atoms, such as a chlorine atom, $C_1$–$C_4$ alkyl radicals, sulfo radicals, carboxy radicals, $C_1$–$C_4$ monohydroxyalkyl radicals, $C_1$–$C_4$ hydroxyalkoxy radicals, acetylamino($C_1$–$C_4$)alkoxy radicals, mesylamino($C_1$–$C_4$)alkoxy radicals, and carbamoylamino($C_1$–$C_4$)alkoxy radicals; and $R_4$ is chosen from hydrogen and halogen atoms and $C_1$–$C_4$ alkyl radicals.

Examples of the nitrogenous groups of formula (I) include amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium, and ammonium radicals.

Examples of the para-phenylenediamines of formula (I) include para-phenylenediamine, para-tolylenediamine, 2-Chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-Chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylene-diamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, N-(4-aminophenyl)-3-hydroxypyrrolidine, and the addition salts thereof with an acid or an alkaline agent.

Among the para-phenylenediamines of formula (I) above, para-phenylenediamine, para-tolylenediamine, 2-isopropyl-para-phenylenediamine, 2β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-Chloro-para-phenylenediamine, and addition salts thereof with an acid or an alkaline agent may, for example, be used.

(II) As used herein, the term "double bases" is understood to refer to compounds comprising at least two aromatic nuclei bearing at least one group chosen from amino and hydroxyl groups.

Examples of the double bases that may be used as oxidation bases in the liquid dye compositions disclosed herein include compounds corresponding to formula (II) below and addition salts thereof with an acid or an alkaline agent:

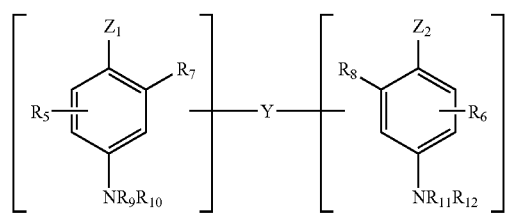

(II)

wherein:

$Z_1$ and $Z_2$, which may be identical or different, are each chosen from hydroxyl and —$NH_2$ radicals which may be substituted with at least one $C_1$–$C_4$ alkyl radical or with a linker arm Y;

linker arm Y is a linear or branched alkylene chain comprising from 1 to 14 carbon atoms, which may be interrupted by or terminated with at least one entity chosen from nitrogenous groups and hetero atoms, such as oxygen, sulfur, and nitrogen atoms, and optionally substituted with at least one radical chosen from hydroxyl and $C_1$–$C_6$ alkoxy radicals;

$R_5$ and $R_6$, which may be identical or different, are each chosen from hydrogen and halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and the linker arm Y; and $R_7$, $R_8$, $R_9$, $R_{10}$, $R_{11}$ and $R_{12}$, which may be identical or different, are each chosen from a hydrogen atom, the linker arm Y, and $C_1$–$C_4$ alkyl radicals; it being understood that the compounds of formula (II) contain only one linker arm Y per molecule.

Examples of the nitrogenous groups of formula (II) include amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium, and ammonium radicals.

Examples of the double bases of formula (II) include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and addition salts thereof with an acid or an alkaline agent.

Among the double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, may be used in the liquid dye compositions disclosed herein.

(III) Para-aminophenols corresponding to formula (III) below, and addition salts thereof with an acid or an alkaline agent:

(III)

wherein:

$R_{13}$ is chosen from a hydrogen atom, a halogen atom, such as fluorine, and $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl, and hydroxy($C_1$–$C_4$)alkylamino($C_1$–$C_4$)alkyl radicals and $R_{14}$ is chosen from a hydrogen atom, a halogen atom, such as fluorine, and $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl, and ($C_1$–$C_4$)alkoxy($C_1$–$C_4$)alkyl radicals.

Examples of the para-aminophenols of formula (III) include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl) phenol, and addition salts thereof with an acid or an alkaline agent.

(IV) Ortho-aminophenols that can be used as oxidation bases in the liquid dye compositions disclosed herein may be chosen, for example, from 2-aminophenol, 2-amino-1-hydroxy-5-methylbenzene, 2-amino-1-hydroxy-6-methylbenzene, 5-acetamido-2-aminophenol, and addition salts thereof with an acid or an alkaline agent.

(V) Heterocyclic bases that may be used as oxidation bases in the liquid dye compositions disclosed herein may be chosen, for example, from pyridine derivatives, pyrimidine derivatives, pyrazole derivatives, and addition salts thereof with an acid or an alkaline agent.

The pyridine derivatives may be chosen from compounds described, for example, in Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and addition salts thereof with an acid or an alkaline agent.

The pyrimidine derivatives may, for example, be chosen from compounds described, for example, in German Patent No. DE 2 359 399 and Japanese Patent Nos. JP 88-169 571 and JP 91-10659 and International Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application No. FR 2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine, 3-amino-5-methyl-7-imidazolylpropylaminopyrazolo[1,5-a]pyrimidine, and tautomeric forms thereof, when a tautomeric equilibrium exists, and addition salts thereof with an acid or an alkaline agent.

The pyrazole derivatives may be chosen from compounds described in Patent Nos. DE 3 843 892, DE 4 133 957 and patent application Ser. Nos. WO 94/08969, WO 94/08970, FR 2 733 749, FR-A-2 817 551, and DE 195 43 988, such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and addition salts thereof with an acid or an alkaline agent.

The oxidation bases may be present in an amount ranging from 0.0005% to 12% by weight, relative to the total weight of the liquid dye composition and, for example, from 0.005% to 8% by weight relative to the total weight of the liquid dye composition.

The couplers may be chosen, for example, from those generally used in the dyeing of human keratin fibers.

Examples of the couplers include meta-aminophenols, meta-phenylenediamines, meta-diphenols, naphthols, heterocyclic couplers, such as indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and addition salts thereof with an acid or an alkaline agent.

The couplers may, for example, be chosen from 2,4-diamino-1-(β-hydroxyethyloxy)benzene, 2-methyl-5-aminophenol, 5-N-(β-hydroxyethyl)amino-2-methylphenol, 3-aminophenol, 2chloro-3-amino-6-methylphenol, 1,3-dihydroxybenzene, 1,3-dihydroxy-2-methylbenzene, 4chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2–c]-1,2,4-triazole, 2,6-dimethylpyrazolo[1,5-b]-1,2,4-triazole, and addition salts thereof with an acid or an alkaline agent.

When present, the couplers may be present in an amount ranging from 0.0001% to 10% by weight, relative to the total weight of the liquid dye composition, and, for example, from 0.005% to 5% by weight, relative to the total weight of the liquid dye composition.

The addition salts with an acid of the oxidation bases and couplers may, for example, be chosen from hydrochlorides, hydrobromides, sulfates, citrates, succinates, tartrates, tosylates, benzenesulfonates, lactates, and acetates.

The addition salts with an alkaline agent may be chosen from addition salts with alkali metals or alkaline earth metals, with ammonia, with organic amines including alkanolamines and compounds having the following formula:

(IV)

wherein W is a propylene residue optionally substituted with at least one entity chosen from hydroxyl groups and $C_1$–$C_6$ alkyl radicals and $R_a$, $R_b$, $R_c$ and $R_d$, which may be identical or different, are each chosen from a hydrogen atom and $C_1-C_6$ alkyl and $C_1-C_6$ hydroxyalkyl radicals.

The liquid dye composition disclosed herein may also comprise at least one direct dye. The at least one direct dye can be chosen from ionic compounds, for example, cationic compounds. In another embodiment, the at least one direct dye can be chosen from non-ionic compounds.

Examples of the at least one direct dye include nitrobenzene dyes, azo dyes, anthraquinone, naphthoquinone, benzoquinone dyes, indigoid dyes, and triarylmethane-based dyes.

When present, the at least one direct dye may be present in an amount ranging from 0.0005% to 12% by weight, relative to the total weight of the liquid dye composition and, for example, from 0.005% to 6% by weight, relative to the total weight of the liquid dye composition.

In yet another embodiment, the liquid dye composition comprises at least one surfactant chosen from non-ionic, cationic, amphoteric, and zwitterionic surfactants.

The non-ionic surfactants may be chosen from compounds that are well known per se (see, for example, in this respect "Handbook of Surfactants" by M. R. Porter, published by Blackie & Son (Glasgow and London), 1991, pp. 116–178).

Nonlimiting examples of the non-ionic surfactants include polyalkoxylated and polyglycerolated fatty alcohols, alpha-diols, and polyalkoxylated $C_8-C_{18}$ alkylphenols, wherein the number of alkylene oxide (ethylene oxide and/or propylene oxide) groups ranges from 2 to 50, and the number of glycerol groups may, for example, range from 1 to 20.

Further examples of non-ionic surfactants include copolymers of ethylene oxide and of propylene oxide, condensates of ethylene oxide and of propylene oxide with fatty alcohols; polyalkoxylated fatty amides, for example, comprising from 2 to 30 mol of alkylene oxide, for example, ethylene oxide; polyglycerolated fatty amides comprising an average of 1 to 5 and, for example, 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides, such as $(C_{10}-C_{14})$ alkylamine oxides and N-acylaminopropylmorpholine oxides.

It should be noted that the above-mentioned fatty compounds usually comprise at least one radical chosen from linear and branched, saturated and unsaturated $C_7-C_{30}$ and, for example, $C_7-C_{18}$ hydrocarbon-based radicals.

The amphoteric and zwitterionic surfactants may, for example, be chosen from aliphatic secondary and tertiary amine derivatives wherein the aliphatic radical is chosen from linear and branched chains comprising from 7 to 18 carbon atoms and comprising at least one water-soluble anionic group (for example, the at least one water-soluble anionic group may be chosen from carboxylate, sulfonate, sulfate, phosphate, and phosphonate groups); mention may also be made of $(C_3-C_{20})$alkylbetaines, sulfobetaines, $(C_8-C_{20})$alkylamido$(C_1-C_6)$alkylbetaines, and $(C_8-C_{20})$ alkylamido$(C_1-C_6)$alkylsulfobetaines.

For example, among the amine derivatives, the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures (V) and (VI):

wherein:
R is chosen from alkyl radicals derived from acid R—COOH present in hydrolysed coconut oil and heptyl, nonyl, and undecyl radicals;
R' is a β-hydroxyethyl group; and
R'' is a carboxymethyl group; and

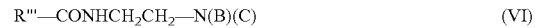

wherein:
B is chosen from —CH$_2$CH$_2$OX' groups;
C is chosen from —(CH$_2$)$_z$—Y' groups, wherein z=1 or 2;
X' is chosen from —CH$_2$CH$_2$—COOH group and a hydrogen atom;
Y' is chosen from —COOH and —CH$_2$—CHOH—SO$_3$H radicals; and
R''' is chosen from alkyl radicals of an acid R'''—COOH present in coconut oil and in hydrolysed linseed oil; alkyl radicals, for example, $C_7-C_{18}$, such as $C_7$, $C_9$, $C_{11}$ and $C_{13}$, a $C_{17}$ alkyl radicals and an iso form thereof, and an unsaturated $C_{17}$ radical.

These compounds are classified in the CTFA dictionary, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylamphodipropionate, lauroamphodipropionic acid, and cocoamphodipropionic acid.

For example, cocoamphodiacetate sold under the trade name Miranol® C2M Concentrate by the company Rhodia Chimie may be used.

The cationic surfactants may be chosen from primary, secondary, and tertiary, optionally polyoxyalkylenated fatty amine salts, such as $C_7-C_{30}$ and, for example, $C_7-C_{18}$; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and amine oxides of cationic nature.

If present, the at least one surfactant may be present in an amount ranging from 0.01% to 40% by weight, relative to the total weight of the liquid dye composition and, for example, from 0.1% to 30% by weight, relative to the total weight of the liquid dye composition.

The liquid dye composition may also comprise at least one thickener chosen, for example, from optionally polyalkoxylated $C_8-C_{30}$ fatty acid amides, and polymers, and, for example, from nonionic, anionic, amphoteric, and cationic associative polymers.

If present, the at least one thickener is present in an amount ranging from 0.05% to 20% by weight, relative to the total weight of the liquid dye composition and, for example, from 0.1% to 15% by weight, relative to the total weight of the liquid dye composition.

The liquid dye composition may also comprise at least one agent chosen from reducing agents and antioxidants chosen, for example, from sodium sulfite, thioglycolic acid, thiolactic acid, sodium bisulfite, dehydroascorbic acid, hydroquinone, 2-methylhydroquinone, tert-butylhydroquinone, and homogentisic acid.

If the at least one agent is used, it may be present in an amount ranging from 0.05% to 3% by weight, relative to the weight of the liquid dye composition.

The liquid dye composition may further comprise at least one additive chosen from those conventionally used in the field, for example, cationic and amphoteric substantive polymers; anionic, nonionic and cationic associative polymers; sequestering agents, such as EDTA and etidronic acid; UV-screening agents; waxes; volatile and non-volatile, cyclic, linear, and branched, organomodified (for example, with at least one amine group) and non-organomodified silicones; preserving agents; ceramides, pseudoceramides; plant, mineral, and synthetic oils; vitamins and provitamins, for example, panthenol; opacifiers; and fragrances, etc.

The pH of the liquid dye composition ranges from 4 to 11.

It may be adjusted to the desired value using acidified or basifying agents usually used in the field.

The acidifying agents may, for example, be chosen from mineral and organic acids, such as hydrochloric acid; orthophosphoric acid; sulfuric acid; carboxylic acids, such as acetic acid, tartaric acid, citric acid and lactic acid; and sulfonic acids.

The basifying agents may, for example, be chosen from aqueous ammonia; alkaline carbonates; alkanolamines, such as monoethanolamine, diethanolamine and triethanolamine and derivatives thereof; sodium hydroxide; potassium hydroxide; and compounds of formula (IV) described herein.

One embodiment disclosed herein relates to a ready-to-use composition comprising the liquid dye composition that has just been described and at least one oxidizing agent.

For example, the at least one oxidizing agent may be chosen from hydrogen peroxide; urea peroxide; alkali metal bromates; ferricyanides; persalts, such as perborates and persulfates; and enzymes, such as peroxidases and two- and four-electron oxidoreductases.

In one embodiment, hydrogen peroxide may be used.

The at least one oxidizing agent may comprise a hydrogen peroxide solution whose titre may range, for example, from 1 to 40 volumes and, further, for example, from 5 to 40 volumes.

The pH of the ready-to-use composition may, for example, range from 4 to 11 and may be adjusted, if necessary, using an acidifying or basifying agent.

Further, the ready-to-use composition may, for example, be in the form of a composition of higher viscosity than that of the liquid dye composition.

In one embodiment, the ready-to-use composition may have the appearance of a gel.

Disclosed herein is also a process for dyeing human keratin fibers comprising applying to the fibers (a) at least one liquid dye composition disclosed herein and (b) at least one oxidizing composition comprising at least one oxidizing agent; wherein the at least one oxidizing composition is mixed at the time of application with the at least one liquid dye composition or is applied sequentially without intermediate rinsing.

The at least one oxidizing composition comprises, in a medium that is suitable for dyeing, at least one oxidizing agent.

As used herein, the term "human keratin fibers" means hair, eyelashes, eyebrows, and moustache.

The dyeing process is performed at conventional temperatures, for example, ranging from room temperature (15 to 25° C.) to 80° C. and, for example, from 15 to 40° C.

Moreover, the at least one liquid dye composition and the at least one oxidizing composition may be applied for a time period sufficient to develop a desired coloration. The time period may range from 3 to 60 minutes and, for example, from 5 to 40 minutes.

Once the leave-in time period has passed, the fibers may be rinsed, optionally washed with shampoo, rinsed, and then dried.

Yet another embodiment disclosed herein relates to a dyeing process comprising, separately storing the at least one liquid dye composition disclosed herein and the at least one oxidizing composition;

mixing the at least one liquid dye composition together with the at least one oxidizing composition at the time of application;

applying the mixture to keratin fibers;

leaving the mixture on the fibers for a time period that is sufficient to develop a desired coloration;

rinsing the fibers, optionally washing the fibers with shampoo, rinsing the fibers again and drying the fibers.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, the numerical values set forth in the specific examples are reported as precisely as possible. Any numerical value, however, inherently contain certain errors necessarily resulting from the standard deviation found in their respective testing measurements. The following examples are intended to illustrate the present disclosure without limiting the scope as a result.

EXAMPLE 1

The following composition was prepared (the amounts are given as % of active material):

| | |
|---|---|
| Oxyethylenated (3 EO) lauryl alcohol | 6 |
| Oxyethylenated (2 EO) lauryl alcohol | 4 |
| Oxyethylenated (5 EO) decyl alcohol | 9 |
| Carboxylic acid alkyl ether monoethanolamide (C13/C15 70/30 50% linear) (2EO) | 12 |
| Diethylaminopropyl laurylaminosuccinamate, sodium salt, as an aqueous solution | 2.5 |
| Denatured 96-degree ethyl alcohol | 4 |
| Deodorized 2-methyl-1,3-propanediol | 13 |
| Propylene glycol | 5 |
| 1-Methyl-2-hydroxy-4-aminobenzene | 2.5 |
| 1,3-Dihydroxybenzene (resorcinol) | 0.01 |
| 1-Hydroxy-4-aminobenzene | 0.86 |
| 1,4-Diaminobenzene | 0.95 |
| 3-Methyl-1-phenyl-5-pyrazolone | 0.15 |
| 1-Methyl-2-hydroxy-4-beta-hydroxyethylaminobenzene | 0.47 |
| Diethyldimethylethylenediamine/1,3-dibromopropylene polycondensate as an aqueous 50% solution | 2.5 |
| Pure monoethanolamine | 3.5 |
| Reducing agent, antioxidant | qs |
| Sequestering agent | qs |
| Fragrance | 0.5 |
| Deionized water | qs 100 |

The composition was clear and stable.

The composition was mixed with a 20-volumes aqueous hydrogen peroxide solution and then applied to a lock of natural hair containing 90% white hair. The bath ratio was 1/10.

After a leave-in time of 20 minutes, the lock was shampooed, rinsed and then dried. The lock obtained was dyed red.

EXAMPLE 2

The following composition was prepared (the amounts are given as % of active material):

| | |
|---|---|
| Polyglycerolated (4 PG) oleyl alcohol | 3.9 |
| Oxyethylenated (3 EO) decyl alcohol | 8.1 |
| Oxyethylenated (5 EO) decyl alcohol | 7.2 |
| Carboxylic acid alkyl ether monoethanolamide (C13/C15 70/30 50% linear) (2EO) | 10 |
| Diethylaminopropyl laurylaminosuccinamate, sodium salt, as an aqueous solution | 2.5 |
| Deodorized 2-methyl-1,3-propanediol | 12 |
| Propylene glycol | 10 |
| 1-Methyl-2-hydroxy-4-aminobenzene | 1.2 |
| 1,3-Dihydroxybenzene (resorcinol) | 0.094 |
| 1-Hydroxy-4-aminobenzene | 0.24 |
| 1,4-Diaminobenzene | 0.3 |
| 3-Methyl-1-phenyl-5-pyrazolone | 0.15 |
| 1-Methyl-2-hydroxy-4-beta-hydroxyethylaminobenzene | 0.18 |
| 6-Hydroxyindole | 0.05 |
| Diethyldimethylethylenediamine/1,3-dibromopropylene polycondensate as an aqueous 50% solution | 1.5 |
| Pure monoethanolamine | 3.4 |
| Reducing agent, antioxidant | qs |
| Sequestering agent | qs |
| Fragrance | 0.5 |
| Deionized water | qs 100 |

The composition was clear and stable.

The composition was mixed with a 20-volumes aqueous hydrogen peroxide solution and then applied to a lock of natural hair containing 90% white hair. The bath ratio was 1/10.

After a leave-in time of 20 minutes, the lock was shampooed, rinsed and then dried. The lock obtained was dyed red.

What is claimed is:

1. A liquid dye composition comprising at least one oxidation dye and 2-methyl-1,3-propanediol, wherein the liquid dye composition is free of fatty acids and of fatty acid salts.

2. The liquid dye composition according to claim 1, wherein the 2-methyl-1,3-propanediol is present in an amount ranging from 0.5% to 20% by weight, relative to the total weight of the liquid dye composition.

3. The liquid dye composition according to claim 2, wherein the 2-methyl-1,3-propanediol is present in an amount ranging from 5% to 20% by weight, relative to the total weight of the liquid dye composition.

4. The liquid dye composition according to claim 3, wherein the 2-methyl-1,3-propanediol is present in an amount ranging from 10% to 18% by weight, relative to the total weight of the liquid dye composition.

5. The liquid dye composition according to claim 1, wherein the liquid dye composition has a viscosity of less than 150 cPs.

6. The liquid dye composition according to claim 1, wherein the liquid dye composition is a clear liquid.

7. The liquid dye composition according to claim 1, wherein the liquid dye composition has a turbidity ranging from 60 to 600 NTU.

8. The liquid dye composition according to claim 7, wherein the liquid dye composition has a turbidity ranging from 70 to 400 NTU.

9. The liquid dye composition according to claim 1, further comprising at least one polyol chosen from:
   polyols comprising at least two hydroxyl radicals, other than 2-methyl-1,3-propanediol and
   polyol monoethers and polyol polyethers,
wherein the polyols comprising at least two hydroxyl radicals and the polyol portion of the polyol monoethers and polyethers comprise at least one radical chosen from saturated and unsaturated, linear and branched hydrocarbon-based radicals comprising from 3 to 50 carbon atoms, optionally interrupted with at least one oxygen atom.

10. The liquid dye composition according to claim 9, wherein the at least one radical comprises from 3 to 10 carbon atoms.

11. The liquid dye composition according to claim 10, wherein the at least one polyol is chosen from pinacol, glycerol, 1,2,3-butanetriol, 3-methyl-1,3,5-pentanetriol, 1,2,4-butanetriol, propylene glycol, dipropylene glycol, 1,5-pentanediol, 3-methyl-1,5-pentanediol, neopentyl glycol, isoprene glycol, and hexylene glycol.

12. The liquid dye composition according to claim 11, wherein the at least one polyol is chosen from glycerol, propylene glycol, dipropylene glycol, and hexylene glycol.

13. The liquid dye composition according to claim 9, wherein the at least one polyol is present in an amount such that the weight ratio of the 2-methyl-1,3-propanediol to the at least one polyol is greater than 1.

14. The liquid dye composition according to claim 13, wherein the at least one polyol is present in an amount such that the weight ratio of the 2-methyl-1,3-propanediol to the at least one polyol is less than or equal to 10.

15. The liquid dye composition according to claim 1, further comprising at least one short-chain monoalcohol.

16. The liquid dye composition according to claim 15, wherein the at least one short-chain monoalcohol is present in an amount ranging from 0.1% to 20% by weight, relative to the total weight of the liquid dye composition.

17. The liquid dye composition according to claim 1, wherein the at least one oxidation dye is chosen from at least one oxidation base and at least one coupler.

18. The liquid dye composition according to claim 17, wherein the at least one oxidation base is chosen from ortho-phenylenediamines, para-phenylenediamines, double bases, ortho-aminophenols, para-aminophenols, heterocyclic bases, and addition salts thereof with an acid or an alkaline agent.

19. The liquid dye composition according to claim 18, wherein the at least one oxidation base is present in an amount ranging from 0.0005% to 12% by weight, relative to the total weight of the liquid dye composition.

20. The liquid dye composition according to claim 17, wherein the at least one coupler is chosen from meta-aminophenols, meta-phenylenediamines, meta-diphenols, naphthols, heterocyclic couplers, and addition salts thereof with an acid or an alkaline agent.

21. The liquid dye composition according to claim 20, wherein the at least one coupler is present in an amount ranging from 0.0001% to 10% by weight, relative to the total weight of the liquid dye composition.

22. The liquid dye composition according to claim 1, further comprising at least one direct dye.

23. The liquid dye composition according to claim 22, wherein the at least one direct dye is chosen from nitrobenzene dyes, azo dyes, anthraquinone dyes, naphthoquinone dyes, benzoquinone dyes, indigoid dyes, and triarylmethane-based dyes.

24. The liquid dye composition according to claim 23, wherein the at least one direct dye is present in an amount ranging from 0.0005% to 12% by weight, relative to the total weight of the liquid dye composition.

25. The liquid dye composition according to claim 1, further comprising at least one surfactant chosen from nonionic, cationic, amphoteric, and zwitterionic surfactants.

26. The liquid dye composition according to claim 25, wherein the at least one surfactant is present in an amount ranging from 0.01% to 40% by weight, relative to the total weight of the liquid dye composition.

27. The liquid dye composition according to claim 1, wherein the liquid dye composition comprises water.

28. A ready-to-use liquid dye composition comprising,
 a liquid dye composition comprising at least one oxidation dye and 2-methyl-1,3-propanediol, wherein the liquid dye composition is free of fatty acids and fatty acid salts and
 at least one oxidizing agent.

29. The ready-to-use composition according to claim 28, wherein the at least one oxidizing agent is chosen from hydrogen peroxide, urea peroxide, alkali metal bromates, alkali metal ferricyanides, persalts, and enzymes.

30. The ready-to-use composition according to claim 29, wherein the persalts are chosen from perborates and persulfates.

31. The ready-to-use composition according to claim 29, wherein the enzymes are chosen from peroxidases and two- and four-electron oxidoreductases.

32. A process for dyeing human keratin fibers comprising applying to the fibers
 (a) at least one liquid dye composition comprising at least one oxidation dye and 2-methyl-1,3-propanediol, wherein the at least one liquid dye composition is free of fatty acids and fatty acid salts and
 (b) at least one oxidizing composition comprising at least one oxidizing agent,
 wherein the at least one oxidizing composition is mixed with the at least one liquid dye composition at the time of application or applied sequentially without intermediate rinsing.

33. A process for dyeing human keratin fibers comprising separately storing
 at least one liquid dye composition comprising at least one oxidation dye and 2-methyl-1,3-propanediol, wherein the at least one liquid dye composition is free of fatty acids and fatty acid salts and
 at least one oxidizing composition comprising at least one oxidizing agent;
 mixing the at least one liquid dye composition together with the at least one oxidizing composition at the time of application;
 applying the mixture to the fibers
 leaving the mixture on the fibers for a time period sufficient to develop a desired coloration;
 rinsing the keratin fibers, optionally washing the fibers with shampoo, rinsing the fibers again and drying the fibers.

34. A multi-compartment device for dyeing human keratin fibers comprising,
 at least one first compartment comprising at least one liquid dye composition comprising at least one oxidation dye and 2-methyl-1,3-propanediol, wherein the at least one liquid dye composition is free of fatty acids and fatty acid salts and
 at least one second compartment comprising at least one oxidizing composition comprising at least one oxidizing agent.

* * * * *